United States Patent
Testa et al.

(10) Patent No.: US 8,357,907 B2
(45) Date of Patent: Jan. 22, 2013

(54) METHOD AND DEVICE FOR REAL-TIME MEASUREMENT OF A LOCAL DOSE UPON BOMBARDMENT OF A TARGET BY HADRONS BY MEANS OF PROMPT GAMMA RAYS

(75) Inventors: Etienne Testa, Lyons (FR); Cedric Ray, Lyons (FR); Nicolas Freud, Lyons (FR)

(73) Assignee: Universite Claude Bernard-Lyon 1, Villeurbanne (FR)

( * ) Notice: Subject to any disclaimer, the term of this patent is extended or adjusted under 35 U.S.C. 154(b) by 97 days.

(21) Appl. No.: 12/991,188

(22) PCT Filed: May 7, 2009

(86) PCT No.: PCT/FR2009/050848
§ 371 (c)(1),
(2), (4) Date: Nov. 5, 2010

(87) PCT Pub. No.: WO2009/141570
PCT Pub. Date: Nov. 26, 2009

(65) Prior Publication Data
US 2011/0057110 A1    Mar. 10, 2011

(30) Foreign Application Priority Data
May 7, 2008   (FR) ...................................... 08 53038

(51) Int. Cl.
*G01T 1/29*   (2006.01)
*G01T 1/02*   (2006.01)
(52) U.S. Cl. ................................. 250/370.07
(58) Field of Classification Search .............. 250/370.07
See application file for complete search history.

(56) References Cited

U.S. PATENT DOCUMENTS 5,665,971 A * 9/1997 Chen et al. .................. 250/385.1
2006/0203967 A1* 9/2006 Nilsson ......................... 378/207
(Continued)

FOREIGN PATENT DOCUMENTS
KR          100783506 B1    12/2007

OTHER PUBLICATIONS

C.H. Min, J.W. Kim, M.Y. Youn, C.H. Kim, "Determination of Distal Dose Edge Location by Measuring Right-Angled Prompt-Gamma Rays from a 38 MeV Proton Beam," ScienceDirect, Nuclear Instruments and Methods in Physics Research A 580 (2007) 562-565.

(Continued)

*Primary Examiner* — Marcus Taningco
(74) *Attorney, Agent, or Firm* — Gardere Wynne Sewell LLP; Andre M. Szuwalski

(57) ABSTRACT

A method for real-time measurement of a local dose received by a region of a target upon bombardment of the target by an incident beam of hadrons generates at least prompt gamma rays and neutrons. The particles emitted by the target are measured by collimating the region of the target and by placing a detector at a distance L from the region of the target to be measured. The detector is linked to a device for particle energy and time-of-flight measurement, in which the number of prompt gamma rays received by the detector is determined by selecting the recorded events, and a two-directional charged-particle detection system, placed in the beam of incident hadrons before the target, is used so as to obtain the transverse position of the incident hadrons in order to provide spatial information about the prompt gamma rays.

29 Claims, 4 Drawing Sheets

U.S. PATENT DOCUMENTS

2007/0228305 A1* 10/2007 Keppel et al. .............. 250/505.1

OTHER PUBLICATIONS

K. Parodi, P. Crespo, H. Eickhoff, T. Haberrer, J. Pawelke, D. Schardt, W. Enghardt, "Random Coincidences During In-Beam PET Measurements at Microbunched Therapeutic Ion Beams," ScienceDirect, Nuclear Instruments and Methods in Physics Research A 545 (2005) 446-458.

D. Schardt, "Tumor Therapy With High-Energy Carbon Ion Beams," ScienceDirect, Nuclear Physics A 787 (2007) 633c-641c.

D. Schardt, H. Iwase, R.S. Simon, K. Gunzert-Marx, "Experimental Investigation of Secondary Fast Neutrons Produced in Carbon Ion Radiotherapy," Proceedings of Science, International Workshop on Fast Neutron Detectors, University of Cape Town, South Africa, Apr. 3-6, 2006, pp. 1-6.

Min Chul-Hee et al: "Prompt gamma measurements for locating the dose falloff region in the proton therapy" Applied Physics Letters, AIP, American Institute of Physics, Melville, NY, vol. 89, No. 18, Nov. 2, 2006, pp. 183517-183517, XP012086792 ISSN: 0003-6951 cited in the application abstract; figures; p. 1, left-hand column, line 26-right-hand column, line 35; p. 2, right-hand column, line 4-line 7.

Scroggs R J et al: "A multicrystal gamma-ray spectrometer with time-of-flight rejection of neutron-induced background" International Symposium on Plasma Phenomena and Measurement Oct. 1963 San Diego, CA, USA, vol. NS-11, No. 1 Jan. 1964, pp. 365-373, XP002513651; IEEE Transactions on Nuclear Science USA abstract; figures; p. 366, right-hand column, line 5-line 28; p. 367, right-hand column, line 1-line 11.

Paulo Crespo et al: "Direct time-of-flight for quantitative, real-time in-beam PET: a concept and feasibility study; Direct time-of-flight for quantitative, real-time in-beam PET" Physics in Medicine and Biology, Taylor and Francis Ltd. London, GB, vol. 52, No. 23, Dec. 7, 2007, pp. 6795-6811, XP020127262; ISSN: 0031-9155 abstract; figures; p. 6797, paragraph 2-p. 6799, paragraph 2.

Abstract of KR 100783506 published Dec. 11, 2007 (translated into English).

International Search Report mailed Dec. 3, 2009 for PCT/FR2009/050848 filed May 7, 2009.

* cited by examiner

METHOD AND DEVICE FOR REAL-TIME MEASUREMENT OF A LOCAL DOSE UPON BOMBARDMENT OF A TARGET BY HADRONS BY MEANS OF PROMPT GAMMA RAYS

PRIORITY CLAIM

This application is a 371 filing from PCT/FR2009/050848 filed May 7, 2009, which claims priority from French Application for Patent No. 08-53038 filed May 7, 2008, the disclosures of which are hereby incorporated by reference.

TECHNICAL FIELD

The present invention pertains to a method and device for real-time measurement of a local dose during the bombardment of a target by hadrons. It applies in particular to the treatment of patients using hadrons, termed hadrontherapy.

BACKGROUND

Hadrontherapy was proposed by Robert R. Wilson in 1946 and is based on the energy deposition characteristics of charged ions in matter. It is aimed in particular at improving the treatment of cancers by virtue of excellent ballistic precision and optimal biological effectiveness, close to 1 in healthy tissues and of the order of 2 to 3 in the tumoral volume (the biological effectiveness of a radiation is defined as the ratio of the doses with X rays and with the relevant radiation so as to obtain one and the same biological effect, typically a survival rate for a cellular population of 10%).

Indeed, in contradistinction to conventional radiations, such as photons (X or gamma) or electrons, for which the profile of the dose delivered to the tissues decreases progressively with depth traversed, that of ions allows a high dose deposition at the end of the track (dubbed a Bragg peak) whereas the dose deposited upstream (corresponding to the so-called plateau region) is much lower. The depth-wise position of the Bragg peak, which is controlled by the incident energy of the beam of charged hadrons, may be modified, thus making it possible to deposit the maximum energy within a circumscribed target volume, in particular a tumor, while sparing the healthy tissues upstream and downstream.

In a manner known per se the ionized hadrons are accelerated by a cyclotron or a synchrotron and the energy of the particle on exiting the accelerator determines the depth of penetration and the position of the maximum biological effectiveness of the irradiation.

By virtue of these properties, allied with weak lateral spreading, the dose deposited in the tissues by charged hadrons may be confined with markedly greater precision than in conventional radiotherapy.

Among the hadrons, light hadrons such as protons or carbon ions are preferably chosen. Carbon ions are particularly advantageous since they exhibit substantially better ballistics than those of protons (less lateral dispersion) and optimal biological effectiveness.

The interaction of the hadrons with the tissues may, when there is inelastic collision between the projectile and target nuclei, create hadron fragmentation phenomena which produce, in particular, unstable nuclei, gamma radiations and neutrons.

For ease of speech, the term "gamma" may be employed to denote a gamma ray.

According to a known method, the emission of positions (for example emitted by $^{11}C$ nuclei in the case of a beam of $^{12}C^{6+}$ ions), is used to measure and/or visualize the dose distribution arising from the interaction between the hadrons and the target. It is in particular possible to use Position Emission Tomography (PET) techniques to this end. However, this technique exhibits the drawback of being an a posteriori measurement which does not make it possible to follow the evolution of the doses received during treatment.

Furthermore, it has been noted that the distribution of the position-emitting particles in the target cannot always be reliably correlated with the dose distribution in the target.

In order to alleviate these drawbacks, a technique for measuring prompt gamma rays has been proposed by Min et al. for controlling the track of the protons during irradiation (Chul-Hee Min and Chan Hyeong Kim, Min-Young Youn, Jong-Won Kim "Prompt gamma measurements for locating the dose falloff region in the proton therapy", Applied Physics Letters 89, 183517 (2006)).

According to this technique, a prompt gamma ray scanner is implemented, which comprises three layers of screens surrounding a detector to form a barrier to the neutrons produced by the nuclear fragmentation. A first layer of paraffin wax moderates the high-energy neutrons, and then a layer of $B_4C$ powder makes it possible to capture a good part of the neutrons and the detector is finally stationed within a layer of lead which blocks the undesired gamma radiations. The total length of the protection layers of such a scanner is about 70 cm which results in a bulky apparatus that is awkward to handle and rather ineffective.

SUMMARY

The aim of the present invention is to remedy the above drawbacks. Consequently, the aim of the invention is to propose a measurement method, in particular for hadrontherapy, which allows real-time local measurement and ensures easy handling of the means implemented. It is furthermore able to be implemented to measure the spatial distribution (in 2 or 3 dimensions) of local doses received by a plurality of regions of a target during the bombardment of said target by a beam of incident hadrons.

This aim is achieved by the method for real-time measurement of a local dose received by a region of a target during the bombardment of said target by a beam of incident hadrons which leads to a nuclear fragmentation in said target and generates at least prompt gamma radiations and neutrons, where the photons and the particles emitted by the target are measured by collimating the region of the target and by stationing a detector at a distance L from the region to be measured of the target, said detector being associated with photon and particle energy and time-of-flight measurement means, and where the number of prompt gamma rays received by said detector is determined by selecting the recorded events corresponding to particles of energy E, greater than or equal to a threshold energy $E_s$, and then by selecting from among these events those included in a time span dt centered substantially on the travel time taken by the prompt gamma rays to traverse the distance L, and where the distance L is chosen so as to make it possible to discriminate the prompt gamma rays from the neutrons by virtue of their difference in propagation speed and where a bidirectional system for detecting charged particles, stationed in the beam of incident hadrons before the target, is implemented in such a way as to obtain the transverse position of the incident hadrons.

The phrase "the recorded events corresponding to particles of energy E" is understood to mean the events for which the energy deposited in the detector has the energy E mentioned.

The phrase "spatial information about the prompt gamma rays" is understood to mean spatial information about emission sites of said prompt gamma rays.

The bidirectional system for detecting charged particles, stationed in the beam of incident hadrons before the target in such a way as to obtain the transverse position of the incident hadrons, makes it possible to obtain spatial information about the prompt gamma rays.

The detector associated with the particle energy and time-of-flight measurement means forms part of a system for detecting prompt gamma rays also comprising means for processing the signal received by said detector.

By virtue of the use of energy and time-of-flight measurement means combined with the choice of energy domain and of a distance between the detector and the region to be measured of the target allowing discrimination, based on flight time, of prompt gamma rays and neutrons, it is possible to dispense with a significant part of the protection layers required according to the technique of Min et al. It is thus possible to obtain a small-size real-time measurement device that is very easy to handle. The inventors have indeed been able to show that the events logged beyond a threshold energy $E_s$ can be discriminated in terms of flight time so as identify events relating to the detection of prompt gamma rays, thus allowing local measurement of the dose received by a target. Furthermore the bidirectional system for detecting charged particles makes it possible to spatially tag the particle and to determine in particular its transverse position with respect to the beam of incident hadrons. It is thus possible to obtain two- or indeed three-dimensional information relating to the recorded events. A beam profiler may then be chosen from among bidirectional systems for detecting charged particles.

The inventors have been able to show that the position of the bidirectional system for detecting charged particles, stationed in the beam of incident hadrons before the target, is particularly advantageous. Indeed, the transverse position of the ions in the target is substantially the same as that of the ions in the incident beam. This identity of transverse position, to within a few millimeters, makes it possible to simply station the bidirectional detection system in the incident beam and to deduce therefrom information making it possible to locate the point of emission of the prompt gamma ray in the target.

According to another embodiment, a three-dimensional spatial distribution of local doses received by a plurality of regions of a target is measured in real time by spatially displacing the target or the detector in relation respectively to the detector or to the target by implementing the bidirectional system for detecting charged particles, stationed in the beam of incident hadrons before the target in such a way as to obtain the transverse position of the incident hadrons.

A measurement of the doses received by the target at various points of its volume is thus advantageously obtained. Such a measurement allows precise control of a hadrontherapy treatment by virtue of the three-dimensional measurement of the distribution of emission of the prompt gamma rays which is tightly correlated with the dose distribution. In this embodiment, the system for detecting the prompt gamma rays is associated with a charged-particle detector, inserted into the beam, upstream of the target. It is thus possible to obtain the three coordinates of the point of emission of the prompt gamma rays: the x and y coordinates (in the plane transverse to the direction of the beam) are provided by the charged-particle detector and the z coordinate is provided by the system for detecting the prompt gamma rays, where z is a direction parallel to that of the beam of incident hadrons.

According to one embodiment of the present invention, a longitudinal distribution of local doses received by a plurality of regions of a target is measured in real time by longitudinally displacing the target or the detector in relation respectively to the detector or to the target.

The term "longitudinal" is intended to mean a direction parallel to that of the beam of incident hadrons. It is thus possible to determine the doses received by the target as a function of the depth of penetration into the target.

According to one embodiment of the present invention, a system for detecting charged particles is stationed in the beam of incident hadrons, said system being able to provide a time-labeling of the incident hadrons, and the corresponding parameters are introduced into the particle time-of-flight measurement means. A temporal correlation is thus established between the system for detecting prompt gamma rays and the system for detecting charged particles for labeling in such a way as to give the flight time measurement means an initial time value from which the counting is performed. This configuration is particularly well suited to the case where the hadrons are emitted in the form of a temporally substantially continuous beam, such as for example provided by a synchrotron. The system for detecting charged particles for labeling may be for example a hodoscope of scintillating fibers or a polycrystalline diamond detector.

The bidirectional system for detecting charged particles, for example a hodoscope, can also serve as labeling system.

It is noted that other means are able to allow time initialization, such as for example utilization of the flux variations of a beam of incident hadrons in particular when this beam is pulsed.

By way of example may be cited ion packet temporal structures that are well suited to such measurements, where the duration of emission of the ion packet is of the order of 1 ns to 5 ns about every ten to a few tens of ns.

According to one embodiment of the present invention, the target is a patient, and the measured region of said target is a cancerous tumor zone (or the healthy tissues situated upstream and downstream).

According to one embodiment of the present invention, the distance L is greater than or equal to 40 cm, for example greater than or equal to 60 cm, and for example less than or equal to 100 cm. A distance of greater than or equal to 40 cm is indeed advantageous since it makes it possible to temporally separate the prompt gamma rays from the neutrons. Indeed, the propagation speed of the prompt gamma rays is 30 cm/ns (nanoseconds) whereas that of the fastest neutrons does not generally exceed that of the incident hadrons (at the maximum ⅔ of the speed of light, i.e. 20 cm/ns). It follows from this that a neutron will take a minimum of 50% more time than the prompt gamma ray to travel the distance L. The time-of-flight measurement means thus make it possible to separate the particles (prompt gammas) to be logged to measure a local dose from the particles (neutrons and gamma rays scattered by the surrounding materials) which may not be precisely correlated with the measurement of a local dose. A temporal difference such as this allows satisfactory selection of the events for consideration. The distance L may be increased, making it possible to boost the time shift between an event related to a prompt gamma ray and an event related to a neutron. However, the detector surface area required in order to keep the number of photons detected constant for a given collimation means is proportional to the distance L. Preferably, a distance L of less than or equal to 1 m will be used.

According to other embodiments of the invention which may be combined together:

the threshold energy $E_s$ is greater than or equal to 500 keV, preferably less than or equal to 5 MeV, or indeed than 2 MeV, for example of the order of 1 MeV;

the time span dt lies between 1 and 15 ns (nanoseconds), for example of the order of 7 ns;

the detector is displaced longitudinally and/or angularly with respect to the target.

According to one embodiment of the present invention, a physical collimator comprising a slit is stationed between the target and the detector associated with the energy and time-of-flight measurement means where the axis of the slit is perpendicular to the beam of incident hadrons. A physical collimator can for example consist of lead blocks. The collimator is stationed for example at a distance D from the target and exhibits a slit of width d. These parameters D and d may be adjusted so as to cover a section of the thickness of the target which defines the spatial resolution of the region to be measured of the target. Preferably this spatial resolution is less than or equal to 1 cm.

According to another embodiment, the detector is associated with electronic collimation means. Such a detector associated with means of electronic collimation can for example form part of a Compton camera.

The invention is also aimed at a method for real-time measurement of a plurality of local doses received in a plurality of regions of a target by implementing one or more of the embodiments of the method hereinabove, by virtue of a plurality of detectors associated with energy and time-of-flight measurement means distributed spatially along and/or around the target.

The invention also pertains to a device for real-time measurement of a local dose received by a region of a target during the bombardment of said target by a beam of incident hadrons comprising:

a detector associated with particle energy and time-of-flight measurement means;

means for collimating the region of the target;

means making it possible to select the events corresponding to particles of energy E, greater than a threshold value E, recorded by virtue of the detector;

means making it possible to select from among the latter events those events included in a given time span dt and where the detector is situated at a distance L from the region to be measured of the target chosen in such a way as to make it possible to discriminate prompt gamma rays and neutrons by virtue of their difference in propagation speed;

a bidirectional system for detecting charged particles, stationed in the beam of incident hadrons before the target in such a way as to obtain the transverse position of the incident hadrons.

According to various embodiments of said device which may be combined together:

the distance L is greater than or equal to 40 cm, for example greater than or equal to 60 cm, and for example less than or equal to 100 cm;

the collimation means comprise a physical collimator comprising a slit, said collimator being stationed between the target and the detector associated with the energy and time-of-flight measurement means;

the collimation means comprise electronic collimation means;

the detector and the collimation means and/or the target are stationed on displacement means allowing a longitudinal and/or angular displacement.

The invention is also aimed at a device for real-time measurement of a plurality of local doses received by a plurality of regions of a target during the bombardment of said target by a beam of incident hadrons comprising a plurality of devices according to one or more of the embodiments hereinabove, distributed spatially along and/or around the target.

BRIEF DESCRIPTION OF THE DRAWINGS

The invention will be better understood on reading the description which follows, given solely by way of example and with reference to the appended drawings in which.

DETAILED DESCRIPTION OF THE DRAWINGS

Figure 1:
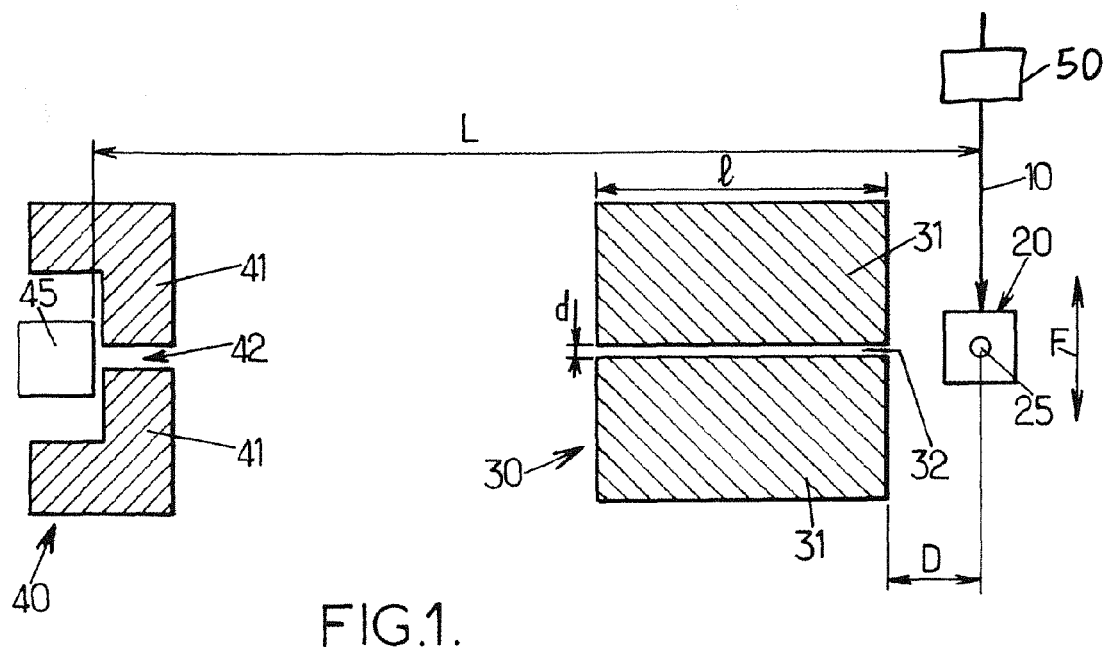
FIG. 1 is a schematic view from above of a device according to the invention.

For the sake of clarity, the various elements represented in FIG. 1 are not necessarily to scale.

FIG. 1 illustrates a schematic view from above of a device according to the invention.

A beam of incident hadrons 10 bombards a target 20. A hodoscope 50 is stationed in the beam of hadrons 10 before the target 20. The hodoscope 50 functions to provide a time labeling of the incident hadrons 10.

The local dose received by the region 25 of the target 20 is measured by virtue of the device according to the invention. The target 20 may be displaced along the arrow F so as to measure other zones of the target.

A collimator 30 is stationed in front of the target 20 at the distance D from it. In the example represented, the collimator consists of two lead blocks 31 of length 1 spaced apart so as to form a slit 32 of width d.

A detection system 40 is placed behind the collimator 30 and comprises a detector 45 placed in alignment with the slit 32 of the collimator. The detector is partially surrounded by lead blocks 41 spaced apart so as to leave an opening 42 facing the detector 45.

According to an exemplary embodiment of the invention:

the detector 45 is a cylindrical detector of NaI (Tl) 5 cm in height and 5 cm in diameter placed at 90° to the beam of incident hadrons 10;

the collimator 30 consists of two lead blocks 31 of length l=20 cm and stationed in such a way as to form a slit of width d=2 mm, orthogonal to the direction of the hadron beam, and situated at the distance D=10 cm from the target;

the distance between the detector 45 and the region 25 to be measured of the target 20 is L=60 cm;

the target is a PMMA ($C_5H_8O_2$) block of cubic shape, where a side measures 10 cm.

Measurements have been performed with the above device under the following conditions:

a 73-MeV/u beam of $^{13}C^{6+}$ ions is used. The beam is pulsed (about 1 ns every 80 ns);

the intensity on the target has been fixed at about 1 nA;

a second detector of NaI(Tl) is used to measure the total dose and is devoid of collimation means and placed at a distance far removed from the target so as to obtain a count rate proportional to the intensity of the beam without being dependent on the position of the target. This detector has been calibrated with a Faraday cage;

the time measurement is carried out with the aid of a time-digital converter which measures the time difference between the logic signal delivered by a threshold-based discriminator synchronized with the high-frequency pulsation of the accelerator, and the logic signal delivered by a constant-fraction discriminator triggered by the analog signal from the detector. The analog signal from this detector is moreover amplified with the aid of a spectroscopy amplifier, and converted by an analog-digital converter. The information relating to the initial time for the count in terms of flight time is discerned by the prompt gamma ray detector 45 and the information relating to the final time is provided by the high-frequency signal from the accelerator in the present case in which a cyclotron is used.

The energy E and time t associated with each event are measured at the same time, as is the number n of events detected by the second NaI(Tl) detector during a trial, which is proportional to the number of incident ions.

Figure 2:
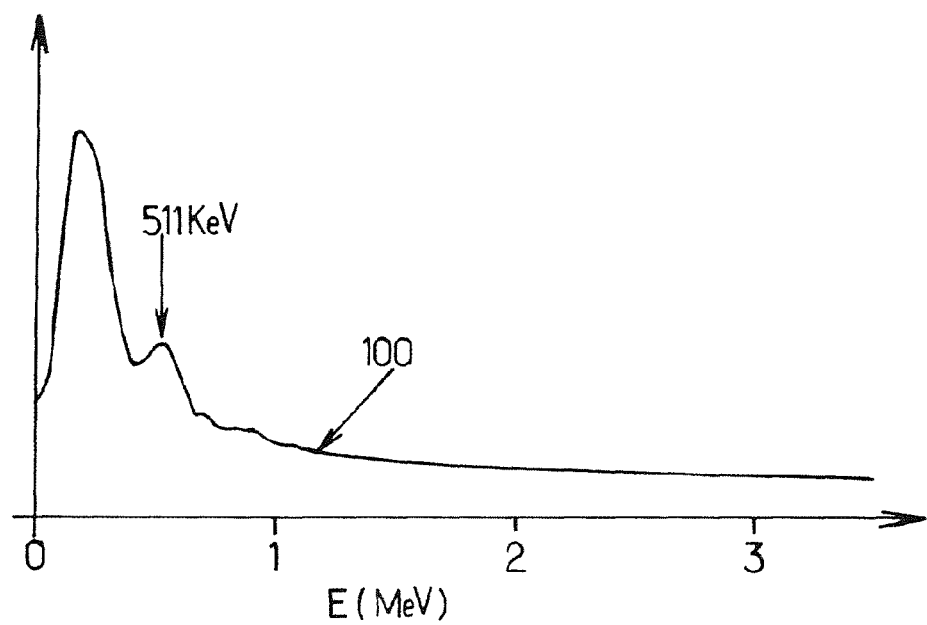
FIG. 2 schematically represents a spectrum in terms of energy deposited in the detector.

FIG. 2 represents a typical energy spectrum 100 obtained during such a trial. It is noted that the shape of the spectrum is substantially independent of the configuration parameters. A single peak is visible at 511 keV which corresponds mainly to the creation of pairs by high-energy photons, followed by a position annihilation.

Figure 3:
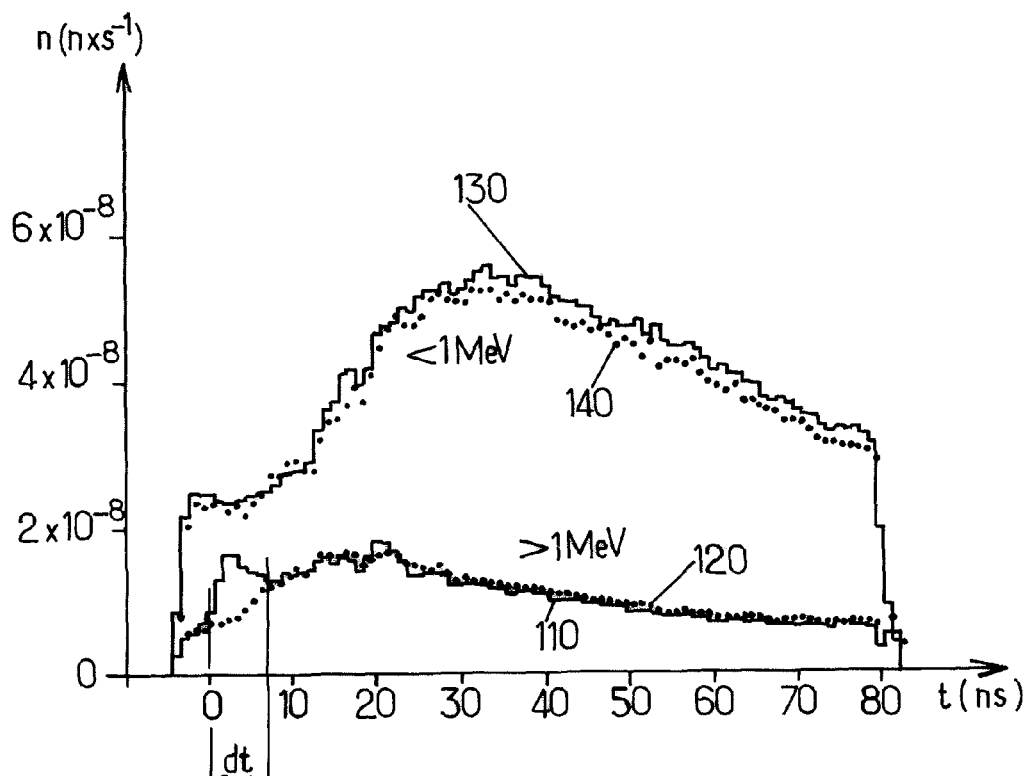
FIG. 3 represents the variation of the number of events detected per 73-MeV/nucleon carbon ion incident in a PMMA target and per interval of 1 ns as a function of time for two energy domains of the detected radiations, such as is measured according to the invention.

FIG. 3 represents time-of-flight spectra, where the number of events per incident ion and per interval of 1 ns (expressed in $ns^{-1}$) is plotted as a function of time t in nanoseconds (ns). The time origin corresponds to the instant of the impact of an ion on the target.

The two spectra 110, 130, shown as solid lines, represent time-of-flight spectra for a measurement where the collimator is aimed at a position in the target situated 8 mm to the rear of the face which receives the beam of incident hadrons. This position corresponds substantially to the middle of the mean track of an ion.

The two spectra 120, 140, marked by dots, represent time-of-flight spectra for a measurement where the collimator is aimed at a position in the target situated 26 mm to the rear of the face which receives the beam of incident hadrons. This position corresponds to a distance situated substantially 12 mm behind the Bragg peak.

For each position, the events whose detected energy is less than 1 MeV (spectra 130 and 140) and those whose energy is greater than 1 MeV (spectra 110 and 120) are logged.

It is noted that the spectra 130, 140 substantially coincide and comparison thereof does not make it possible to identify particular events. It may be thought that, under the present experimental conditions, when the energy is less than 1 MeV, the distribution of the events is totally dominated by neutrons. In contradistinction to the previous spectra, the spectra 110 and 120 differ in a flight time zone denoted dt. It is indeed noted that the number of events logged is much greater for the spectrum 110 as compared with the spectrum 120. These events can without ambiguity be attributed to the counting of the prompt gamma radiation in the target. Indeed, the time span dt corresponds to a time span extending around the time required by a prompt gamma ray to travel the distance L=60 cm, that is to say of the order of 2 ns. It is noted that the measurement makes it possible to log the number of prompt gamma rays with excellent precision by considering the whole set of events over the time span dt and that the signal-to-noise ratio is of the order of 1. It follows from this that it is thus possible to determine a local dose in a target by using selection based both on energy and on flight time.

Figure 4:
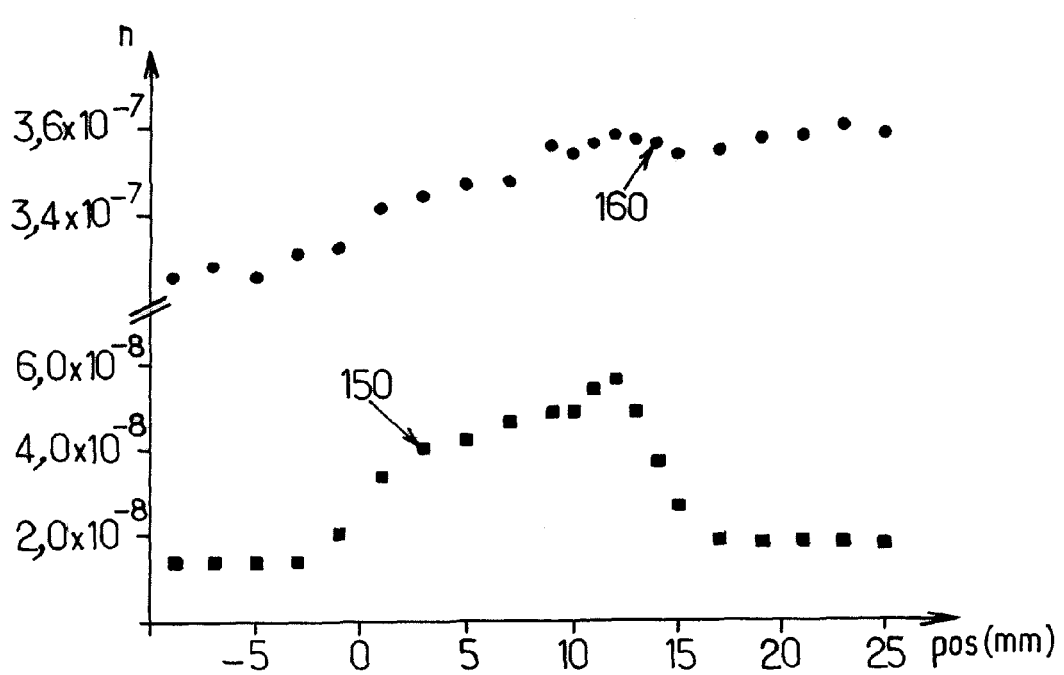
FIG. 4 represents the variation of the number of particles measured as a function of the position of the target, according to the invention.

FIG. 4 represents the variation of the number of events detected using the experimental conditions hereinabove as a function of the distance to the face of the target which receives the hadron beam. The measurements are obtained by displacing the target along the arrow F and by leaving the collimator, detection device assembly in a constant position. The position "pos=0" corresponds to a position of the collimator orthogonal to the hadron beam and looking at the front face of the target, negative positions "pos" correspond to measurements of the surrounding background noise, positive positions "pos" correspond to measurements in the target at a distance "pos" from the front face, where the collimator remains in a position orthogonal to the hadron beam.

The two curves 150 and 160 were obtained after selecting the events whose energy is greater than 1 MeV, under similar acquisition conditions.

Curve 150 depicts the detected events for a count in terms of flight time between 2 and 10 ns. Curve 160 depicts the detected events for a count in terms of flight time at times greater than 10 ns.

It is noted that curve 160 is of substantially continuous variation and the events are attributed to the presence of neutrons whose flight time is at least about 6 ns under the experimental conditions mentioned.

It is noted that curve 150 exhibits a peak in a zone with position lying substantially between 0 and 15 mm. This peak is attributed to the counting of the prompt gamma rays as a function of the thickness traversed in the target. These results are entirely consistent with the observation of the PMMA target which is faded over a depth of 14 mm precisely. It is noted that the peak of curve 150 can be decomposed into a zone of events with moderately rising number, situated between 2 and 10 mm from the front face of the target, followed by a peak centered around 12 to 13 mm from the front face of the target. This peak can be correlated with the Bragg peak of the incident hadron which is at 14 mm.

It is therefore demonstrated that under the conditions of the present invention, it is possible to identify the effects of the Bragg peak in a target and to measure the quantity of associated prompt gamma rays, thus making it possible to obtain a measurement that can be correlated with the quantity of hadrons received in a given zone of a target. The relation between track and energy deposited is very well known in the literature. It is thus possible to obtain the relation between the number of prompt gamma rays and the local dose.

The results reported here and obtained with 73-MeV/nucleon incident ions make it possible to demonstrate that the count rates are compatible with a real-time monitoring system. Moreover, by utilizing the results measured for a selected energy range and for a determined flight time window, it is possible to dispense with a part of the bulky protection devices implemented in the procedure described by Min et al (in particular the neutron shielding). It is thus possible to propose lightweight and compact detectors, able to be associated so as to constitute a set of detectors and to spatially measure with great precision the quantity of prompt gamma rays emitted by a zone of a target and determine the locally received flux of hadrons.

Figure 5:
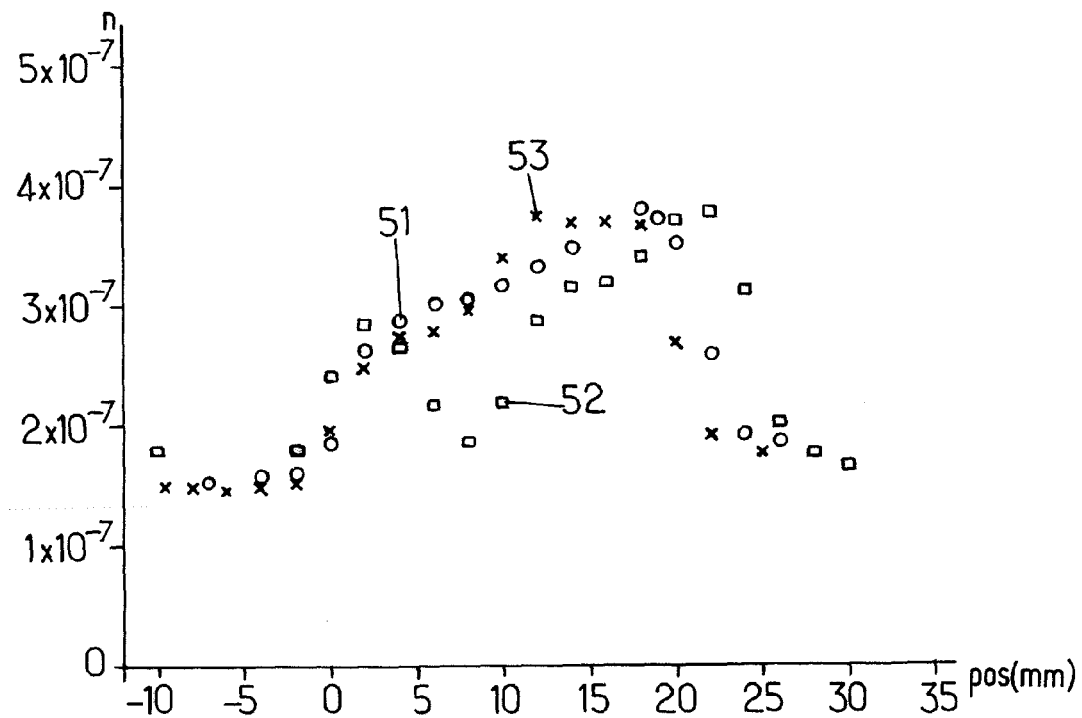
FIGS. 5 and 6 represent the variation of the rate of prompt gamma rays through various targets.
Figure 6:
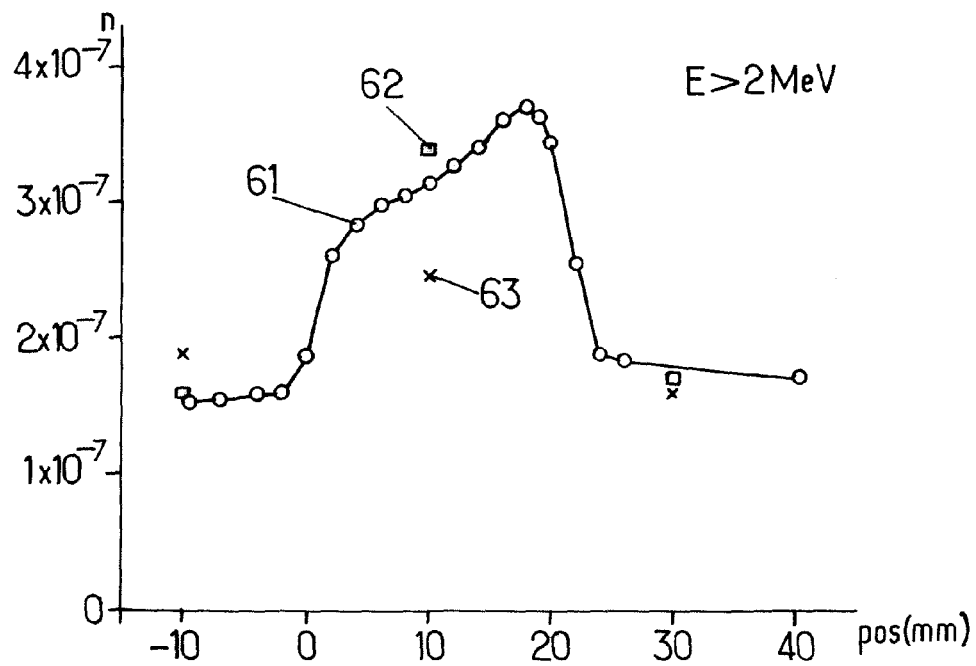

FIGS. 5 and 6 depict the variation of the number of events detected with the previous device under different experimental conditions:

The incident ions are 95-MeV/nucleon $^{12}$C ions and the events selected on the basis of flight time are those whose energy is greater than 2 MeV, obtained at 90° and with a collimation slit width of 2 mm.

The results presented in FIG. 5 were obtained with targets of various materials. The data represented by circles, referenced 51, were obtained with a PMMA target; those represented by squares, referenced 52, with a teflon target (density of 1.9 g/cm$^3$, close to that of a bone); those represented by crosses, referenced 53, with a material equivalent to the lung (density of 0.3 g/cm$^3$).

The front face of the PMMA target is situated in the position pos=0 and extends up to pos=33 mm. The front face of the teflon target is situated in the position pos=10 mm and extends up to pos=12.5 mm. The front face of the target equivalent to the lung is situated in the position pos=6 mm and extends up to pos=12.5 mm.

It is thus demonstrated that the rate of prompt gamma rays depends on the observed material density and that it is possible to locate inhomogeneities in the target traversed by virtue of the procedure according to the invention.

The results presented in FIG. 6 were obtained with PMMA targets of various sizes and shapes. The data represented by circles, referenced 61, were obtained with a cube with sides of 5 cm; those represented by squares, referenced 62, with a cylinder cm in diameter; those represented by crosses, referenced 63, with a cube with sides of 30 cm.

It is noted that the attenuation of the photons in a voluminous target does not cause the signal to vanish. Furthermore when the target is small, the signal-to-noise ratio decreases, but remains sufficiently high to provide real-time information about the track of the ions.

Figure 7:
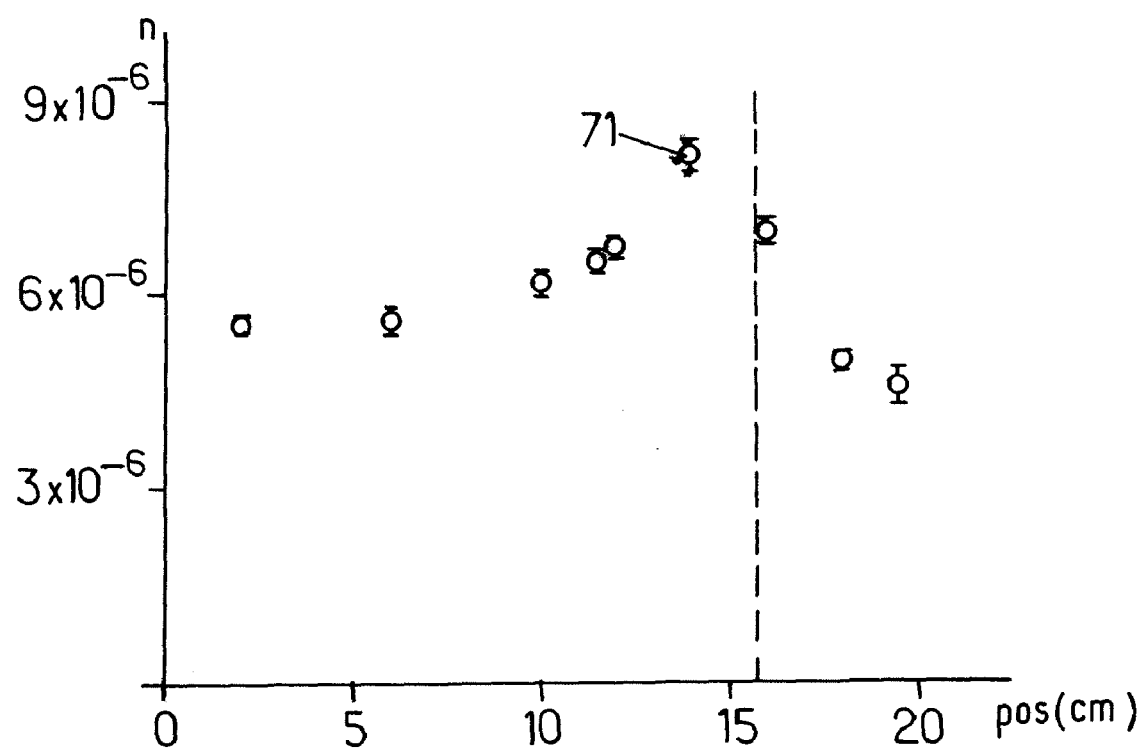
FIG. 7 represents the variation of the rate of prompt gamma rays for 292-MeV/nucleon incident ions.

FIG. 7 depicts experimental data obtained under conditions where the incident ions are 292-MeV/nucleon $^{12}$C ions. The tracks thus obtained are similar to those used in hadrontherapy to reach deep tumors. The events selected on the basis of flight time are those whose energy is greater than 2.5 MeV, the width of the collimation slit is 1 cm and the target is water.

The calculated position of the Bragg peak is represented dashed and the count rates for the prompt gamma rays are represented by circles, referenced 71. The profile thus observed confirms that the measured yields are compatible with on-line and real-time control of a hadrontherapy treatment.

By virtue of the measurement method and/or of the device according to the invention, it is therefore possible to obtain means for real-time control of hadronthrapy, by obtaining a bidirectional, or preferably three-dimensional, distribution of the dose deposited in the patient, with a resolution of the order of a mm.

It may be estimated that the temporal control may be performed on a scale of a second.

It is thus for example possible to interrupt a treatment should the dose be poorly distributed relative to the treatment plan.

It should be noted that diverse detectors may be used to implement the present invention and that variants may be afforded to the structure of the device previously described and to its method of use.

The invention is not limited to these types of embodiment and should be interpreted in a non-limiting manner, encompassing any equivalent embodiment.

The invention claimed is:

1. A method for real-time measurement of a local dose received by a region of a target during the bombardment of said target by an incident beam of hadrons which leads to a nuclear fragmentation in said target and generates at least prompt gamma radiations and neutrons, comprising:
    measuring the particles emitted by the target by collimating the region of the target; and
    receiving prompt gamma ray using a detector stationed at a distance L from the region to be measured of the target, said detector being associated with particle energy and time-of-flight measurement means, and
    determining a number of prompt gamma rays received by said detector by:
        selecting the recorded events corresponding to particles of energy E, greater than or equal to a threshold energy $E_s$, and then
        selecting from among these events those included in a time span dt centered substantially on the travel time taken by the prompt gamma rays to traverse the distance L, and
    where the distance L is chosen so as to make it possible to discriminate the prompt gamma rays from the neutrons by virtue of their difference in propagation speed and
    where a hodoscope for detecting charged particles, stationed in the beam of incident hadrons before the target, is implemented in such a way as to obtain the transverse position of the incident hadrons.

2. The method as claimed in claim 1, wherein a three-dimensional spatial distribution of local doses received by a plurality of regions of a target is measured in real time by spatially displacing the target or the detector in relation respectively to the detector or to the target by implementing said hodoscope for detecting charged particles.

3. The method as claimed in claim 1, wherein a longitudinal distribution of local doses received by a plurality of regions of a target is measured in real time by longitudinally displacing the target or the detector in relation respectively to the detector or to the target.

4. The method as claimed in claim 1, wherein the hodoscope stationed in the beam of incident hadrons provides a time-labeling of the incident hadrons, and the corresponding parameters are introduced into the particle time-of-flight measurement means.

5. The method as claimed in claim 1, wherein the distance L is greater than or equal to 40 cm.

6. The method as claimed in claim 5, wherein the distance L is greater than or equal to 60 cm.

7. The method as claimed in claim 5, wherein the distance L is less than or equal to 100 cm.

8. The method as claimed in claim 1, wherein the threshold energy $E_s$ is greater than or equal to 500 keV.

9. The method as claimed in claim 8, wherein the threshold energy $E_s$ is less than or equal to 5 MeV.

10. The method as claimed in claim 6, wherein the threshold energy $E_s$ is less than or equal to 2 MeV.

11. The method as claimed in claim 8, wherein the threshold energy $E_s$ is of the order of 1 MeV.

12. The method as claimed in claim 1, wherein the time span dt lies between 1 and 15 ns (nanoseconds).

13. The method as claimed in claim 12, wherein the time span dt lies is of the order of 7 ns.

14. The method as claimed in claim 1, wherein a physical collimator comprising a slit is stationed between the target and the detector associated with the energy and time-of-flight measurement means and/or in that the detector associated with the energy and time-of-flight measurement means is associated with means of electronic collimation.

15. The method as claimed in claim 1, wherein the local dose comprises a plurality of local doses received in a plurality of regions of a target and wherein the process of claim 1 is performed by virtue of a plurality of detectors associated with energy and time-of-flight measurement means distributed spatially along and/or around the target.

16. A device for real-time measurement of a local dose received by a region of a target during the bombardment of said target by a beam of incident hadrons comprising:
- a detector associated with particle energy and time-of-flight measurement means,
- means for collimating the region of the target,
- means for making it possible to select the events corresponding to particles of energy E, greater than a threshold value $E_s$ recorded by virtue of said detector,
- means for making it possible to select from among the latter events those events included in a given time span dt and where said detector is situated at a distance L from the region to be measured of the target chosen in such a way as to make it possible to discriminate prompt gamma rays and neutrons by virtue of their difference in propagation speed,
- a hodoscope for detecting charged particles, stationed in the beam of incident hadrons before the target in such a way as to obtain the transverse position of the incident hadrons.

17. The device as claimed in claim 16, wherein the distance L is greater than or equal to 40 cm.

18. The device as claimed in claim 17, wherein the distance L is greater than or equal to 60 cm.

19. The device as claimed in claim 17, wherein the distance L is less than or equal to 100 cm.

20. The device as claimed in claim 16, wherein the collimation means comprise a physical collimator comprising a slit, said collimator being stationed between the target and the detector associated with the energy and time-of-flight measurement means, where the axis of the slit is perpendicular to the beam of incident hadrons and/or in that the collimation means comprise electronic collimation means.

21. The device as claimed in claim 16, wherein the detector associated with the energy and time-of-flight measurement means and the collimation means and/or the target, are stationed on displacement means allowing a longitudinal and/or angular displacement.

22. The device as claimed in claim 16, wherein the local dose comprises a plurality of local doses and the region comprises a plurality of regions of a target, further comprising a plurality of devices as claimed in claim 16, distributed spatially along and/or around the target.

23. The device as claimed in claim 16, wherein the threshold energy $E_s$ is greater than or equal to 500 keV.

24. The device as claimed in claim 23, wherein the threshold energy $E_s$ is less than or equal to 5 MeV.

25. The device as claimed in claim 23, wherein the threshold energy $E_s$ is less than or equal to 2 MeV.

26. The device as claimed in claim 23, wherein the threshold energy $E_s$ is of the order of 1 MeV.

27. The device as claimed in claim 16, wherein the time span dt lies between 1 and 15 ns (nanoseconds).

28. The device as claimed in claim 27, wherein the time span dt is of the order of 7 ns.

29. The device as claimed in claim 16, wherein the hodoscope stationed in the beam of incident hadrons provides a time-labeling of the incident hadrons, and the corresponding parameters are introduced into the particle time-of-flight measurement means.

* * * * *